(12) United States Patent
Glover et al.

(10) Patent No.: US 7,902,416 B2
(45) Date of Patent: Mar. 8, 2011

(54) FLUIDIZED BED REACTOR WITH BACK-MIXING FOR DEHYDROGENATION OF LIGHT PARAFFINS

(75) Inventors: Bryan K. Glover, Algonquin, IL (US); Julie A. Zarraga, Bartlett, IL (US); Michael A. Schultz, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 617 days.

(21) Appl. No.: 11/954,153

(22) Filed: Dec. 11, 2007

(65) Prior Publication Data
US 2008/0161624 A1   Jul. 3, 2008

Related U.S. Application Data

(60) Provisional application No. 60/882,349, filed on Dec. 28, 2006.

(51) Int. Cl.
*C07C 5/333* (2006.01)
(52) U.S. Cl. ......... 585/634; 585/654; 585/659; 585/660; 585/661; 502/308; 422/138; 422/144; 422/146; 122/4 D; 122/7 R
(58) Field of Classification Search .................. 585/634, 585/654, 659, 660, 661; 502/308; 422/138, 422/144, 146; 122/4 D, 7 R
See application file for complete search history.

(56) References Cited

U.S. PATENT DOCUMENTS

| | | | |
|---|---|---|---|
| 4,381,417 A | 4/1983 | Vora et al. | 585/655 |
| 4,613,715 A | 9/1986 | Haskell | |
| 4,951,613 A * | 8/1990 | Harandi et al. | 122/4 D |
| 5,389,342 A | 2/1995 | Savage et al. | |
| 5,436,383 A | 7/1995 | Le Peltier et al. | 585/655 |
| 6,392,113 B1 | 5/2002 | Gartside | 585/654 |
| 2004/0092391 A1 * | 5/2004 | Rokicki et al. | 502/308 |

FOREIGN PATENT DOCUMENTS

WO   WO 2005077867 A2   8/2005

* cited by examiner

*Primary Examiner* — Prem C Singh
(74) *Attorney, Agent, or Firm* — Arthur E. Gooding

(57) ABSTRACT

An improved process and system for the endothermic dehydrogenation of an alkane stream is described. The process and system of the present invention comprise a back-mixed fluidized bed reactor. The alkane stream is dehydrogenated in a single reactor stage by contacting the alkane stream with a back-mixed fluidized bed of catalyst. Deactivated catalyst is withdrawn from the back-mixed fluidized reactor and heated to produce hot regenerated catalyst. The hot regenerated catalyst is returned to the back-mixed fluidized bed reactor at a rate sufficient to maintain the back-mixed fluidized bed reactor at substantially isothermal conditions.

14 Claims, 2 Drawing Sheets

FLUIDIZED BED REACTOR WITH BACK-MIXING FOR DEHYDROGENATION OF LIGHT PARAFFINS

CROSS-REFERENCE TO RELATED APPLICATION

This application claims priority from Provisional Application No. 60/882,349 filed Dec. 28, 2006, the contents of which are hereby incorporated by reference.

FIELD OF THE INVENTION

This invention relates to a catalytic dehydrogenation process and system with improved conversion and selectivity and lower operating and installation costs.

BACKGROUND OF THE INVENTION

The catalytic dehydrogenation of alkanes (paraffin hydrocarbons) to produce alkenes (olefin hydrocarbons) is an important and well known hydrocarbon conversion process in the petroleum refining industry. This is because alkenes are generally useful as intermediates in the production of other more valuable hydrocarbon conversion products. For example, propylene can be used in the production of polymers and propylene glycol, butylenes can be used in the production of high octane motor fuel and isobutylenes can be used to produce methyl-t-butyl ether, a gasoline additive.

The catalytic dehydrogenation of alkanes is an endothermic reaction. The reaction is very fast and reversible and conversion rates are limited by the thermodynamic equilibrium conditions. High temperatures and low pressures favorably displace the reaction toward the formation of alkenes.

Numerous patents describe state of the art systems for the catalytic dehydrogenation of alkanes. For example, U.S. Pat. No. 4,381,417 describes a catalytic dehydrogenation system in which a radial flow reactor is employed and U.S. Pat. No. 5,436,383 describes a catalytic dehydrogenation system in which either a fixed bed, moving bed, or fluid bed reactor can be employed. Because of the fast and endothermic nature of the catalytic alkane dehydrogenation reaction, prior art processes all require multiple reactors or reactor stages to achieve a sufficient yield of alkene product. Additionally, conventional catalytic dehydrogenation systems require multiple heaters to supply the heat of reaction. Typically a preheater and multiple reactor interheaters are used. The interheaters are positioned between the reactors to ensure that at the entrance of each of the reactors, the temperature conditions necessary for the endothermic dehydrogenation reaction are met. In an alternative prior art process, a set of catalytic dehydrogenation reactors are operated in a cyclic non-steady-state mode with regeneration of a catalyst bed every 10 to 30 minutes, as described in U.S. Pat. No. 6,392,113. The catalyst bed is heated during regeneration and this heat is used to carry out the dehydrogenation reaction. Reactors are large and multiple reactors in parallel are needed for large plant sizes. Frequent cycling of the system can lead to operational and maintenance problems and the non-continuous system is less thermally efficient than a continuous process.

It has long been recognized in industry that conventional catalytic dehydrogenation systems suffer from a variety of drawbacks. For example, in conventional catalytic dehydrogenation systems relatively large reactors are necessary to achieve equilibrium conversion. This increases the complexity and capital costs of the catalytic dehydrogenation system. Capital costs are also increased in conventional systems by the need to have multiple reactors. A further drawback is that the high temperatures that are required to shift the equilibria favorably to alkene products also promote rapid deactivation of the catalyst by coking. The high temperatures can also lead to thermal cracking of the alkanes—i.e. undesirable non-selective side reactions resulting in formation of byproducts with a broad range of carbon numbers, which complicates separation of the product stream. The formation of heavy byproducts can foul the reactors, with the result that the catalytic dehydrogenation system has to be shut-down periodically and cleaned. In order to limit the amount of fouling, the heavy byproducts are separated from the unconverted alkane prior to recycle of the unconverted alkane using a front-end distillation column.

SUMMARY OF THE INVENTION

Accordingly, it is an object of the present invention to provide a catalytic dehydrogenation system and process with reduced capital and operating costs and greater conversion and selectivity. It is a further object of the present invention to provide a catalytic dehydrogenation system and process with simplified process design.

We have discovered a catalytic dehydrogenation system and process in which capital and operating costs are reduced, product conversion and selectivity are increased, and process design is simplified by using a back-mixed fluidized bed reactor. In a preferred embodiment of the present invention, an alkane-rich stream is fed to a single reactor stage in which the alkane-rich stream is contacted with a fluidized bed of catalyst. Deactivated catalyst is withdrawn from the reactor and sent to a regenerator where coke is burned off the catalyst to regenerate it. Additional fuel is also burned in the regenerator to raise the temperature of the catalyst. The hot catalyst is then returned to the fluidized bed reactor, providing the heat necessary for the endothermic dehydrogenation of the alkane-rich stream.

The fluidized bed is designed to be highly back-mixed in the fluidized phase. Because the reactor has a highly back-mixed solids phase, the alkanes are not exposed to high temperatures and the fluidized bed is maintained at an essentially isothermal condition. Eliminating exposure to high temperatures reduces selectivity losses due to thermal cracking reactions and the formation of heavy byproducts. As a result, the front-end distillation column used in prior art processes can be eliminated. The formation of light alkane byproducts such as methane, ethane and propane is reduced, leading to an increased yield of the desired alkene. The use of a substantially isothermal fluidized bed reactor obviates the use of multiple reactors and interheaters and thereby reduces capital and operating costs.

DETAILED DESCRIPTION OF THE INVENTION

Figure 1:
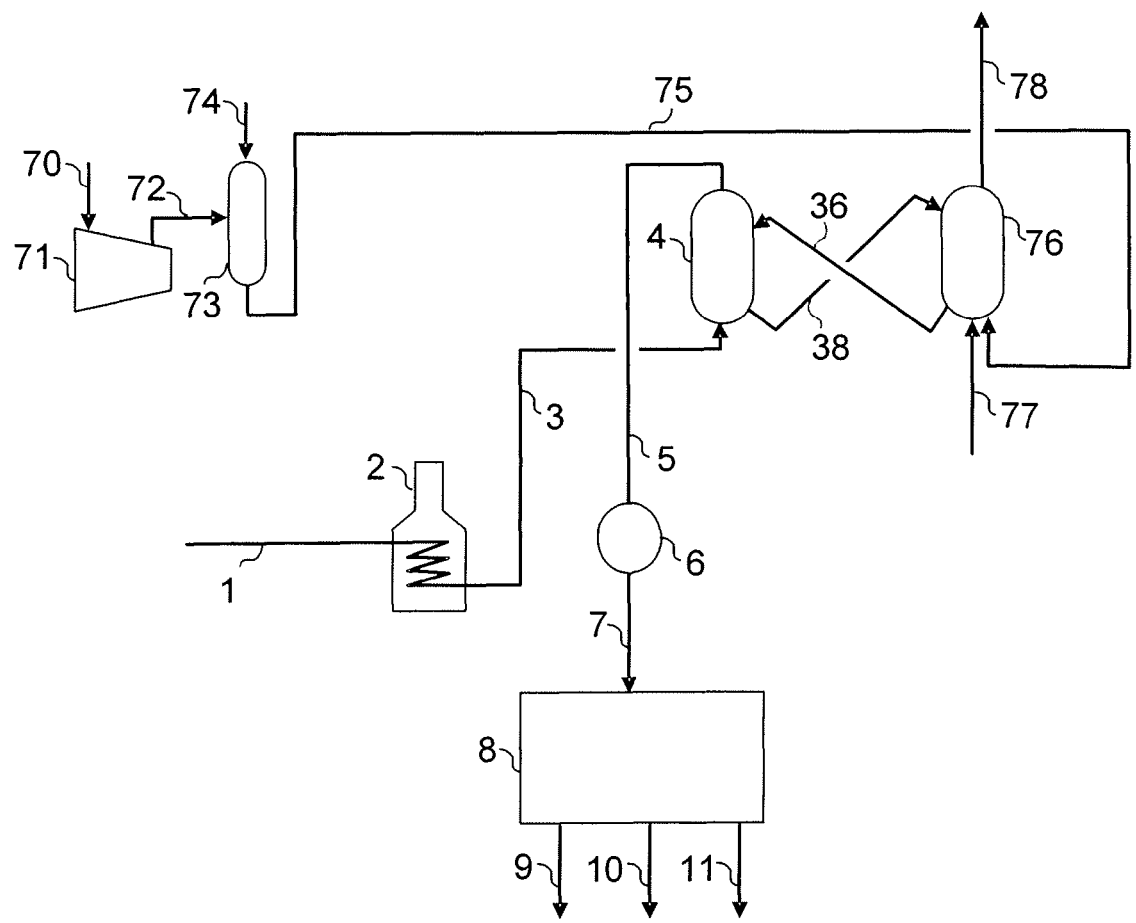
FIG. 1 is a schematic view of a flow scheme of the present invention.

Referring now to FIG. 1, in one embodiment of the process of the invention a feed comprising one or more alkanes enters the process through a line 1. The feed is heated in a furnace 2 and is passed through a line 3 to a back-mixed fluidized bed reactor 4. The feed is heated in the furnace 2 to a reaction temperature. The reaction temperature is preferably in the range from 300° to 700° C. and most preferably about 580° to 620° C. Thus, unlike feeds in prior art processes, the feed in the present invention is not preheated to a temperature well-above the final reaction temperature. The lower feed temperatures utilized in the present invention advantageously reduce or eliminate undesired thermal cracking reactions. This increases the desired product yield. Using lower temperatures also reduces operating costs.

The back-mixed fluidized bed reactor 4 contains a back-mixed fluidized bed of a suitable catalyst for dehydrogenation of alkanes. In a preferred embodiment, the fluidized bed reactor 4 is designed to be highly back-mixed in the fluidized phase; i.e., solids within the back-mixed fluidized bed reactor 4 behave as if they are in a continuously stirred tank reactor (CSTR). It is also preferred that the back-mixed fluidized bed reactor 4 comprises a fast fluidized bed of catalyst. Suitable catalysts are well known to those skilled in the art and typically comprise a support material chosen from the group comprising: alumina, silica, aluminosilicates, aluminophosphates, natural and synthetic zeolites, clays and metal oxides on which is dispersed a metal from the group comprising iron, nickel, chromium, molybdenum, tungsten, palladium, platinum, rhenium and cobalt. The catalyst preferably has a particle size in the range 10 to 500 micrometers and more preferably in the range 20 to 200 micrometers. Use of a fast back-mixed fluidized bed minimizes carbonaceous deposits within the back-mixed fluidized bed reactor 4 and makes the process of the present invention more resistant to coking or fouling than prior art fixed or moving bed processes.

The back-mixed fluidized bed reactor 4 is maintained at a low process pressure, to favor the equilibrium of the alkane dehydrogenation reaction. The low process pressure is preferably in the range from an absolute pressure of 50 kPa to an absolute pressure of 500 kPa and is most preferably about 125 to 250 kPa. A dehydrogenation reactor product is withdrawn from the back-mixed fluidized bed reactor 4 through a line 5 and is cooled by heat exchange in a heat exchange system 6. The heat exchange system 6 may comprise one or more heat exchangers for recovery of heat from the dehydrogenation reactor product for various uses in the process. A cooled dehydrogenation reactor product is withdrawn from the heat exchange system 6 through a line 7 and is sent to a separation section 8. In the separation section 8 the cooled dehydrogenation reactor product is separated into a hydrogen-rich product, an alkane-rich product and an alkene-rich product. The hydrogen-rich product leaves the separation section 8 in a line 9 and is available for sale as hydrogen or for use as a process fuel. The alkane-rich product leaves the separation section 8 in a line 10 and can be recycled to the feed and returned to the line 1, or else can be used as fuel. The alkene-rich product leaves the separation section 8 in a line 11 and is suitable for sale or further processing.

An air stream is drawn via a suction line 70 into an air compressor or blower 71, where it is compressed to form a compressed air stream. The compressed air stream is preferably at a pressure in the range 100 to 3,000 kPa and most preferably in the range 200 to 500 kPa. In one embodiment, the compressed air stream is sent via a line 72 to a precombustor 73, where it meets a fuel stream entering via a line 74 and undergoes a combustion reaction to form a preheated air stream. The energy released from the combustion reaction raises the temperature of the preheated air stream to a preheat temperature. The preheated air stream is sent via a line 75 to a regenerator 76. The regenerator 76 comprises one or more reactors suitable for regenerating the catalyst. The regenerator 76 may comprise a bubbling bed reactor or a fast fluidized bed reactor. In a preferred embodiment of the present invention, the regenerator 76 comprises a single fast fluidized bed reactor. A first supplementary fuel stream may also be fed to the regenerator 76 via a line 77. The preheated air stream reacts with any coke that is deposited on deactivated catalyst contained in the reactor or reactors of the regenerator 76, forming a hot flue gas, which leaves the regenerator 76 and can be vented to atmosphere via a line 78. In an alternative embodiment, the hot flue gas leaving the regenerator 76 may be expanded in a turbine (not shown for clarity) to form a low-pressure flue gas. The low-pressure flue gas is withdrawn from the turbine in a line and is sent to a waste heat boiler for recovery of heat before being vented to the atmosphere via a line. In an alternative embodiment, the hot flue gas leaving the regenerator 76 may be combined with a second supplementary fuel stream and fed to a waste heat boiler (not shown for clarity) for recovery of heat before being vented to atmosphere via a line.

A stream of deactivated catalyst is withdrawn continuously from the back-mixed fluidized bed reactor 4 via a line 38, and is sent to the regenerator 76. A stream of regenerated catalyst is withdrawn continuously from the regenerator 76 via a line 36, and is sent to the back-mixed fluidized bed reactor 4. In one embodiment of the invention, a first product defined as [(catalyst mass flow rate×catalyst specific heat capacity)×(temperature of the hot regenerated catalyst−temperature of the back-mixed fluidized bed of catalyst)] is substantially equal to a second product defined as [moles of the alkane stream converted×molar heat of reaction for dehydrogenation of the alkane stream].

Figure 2:
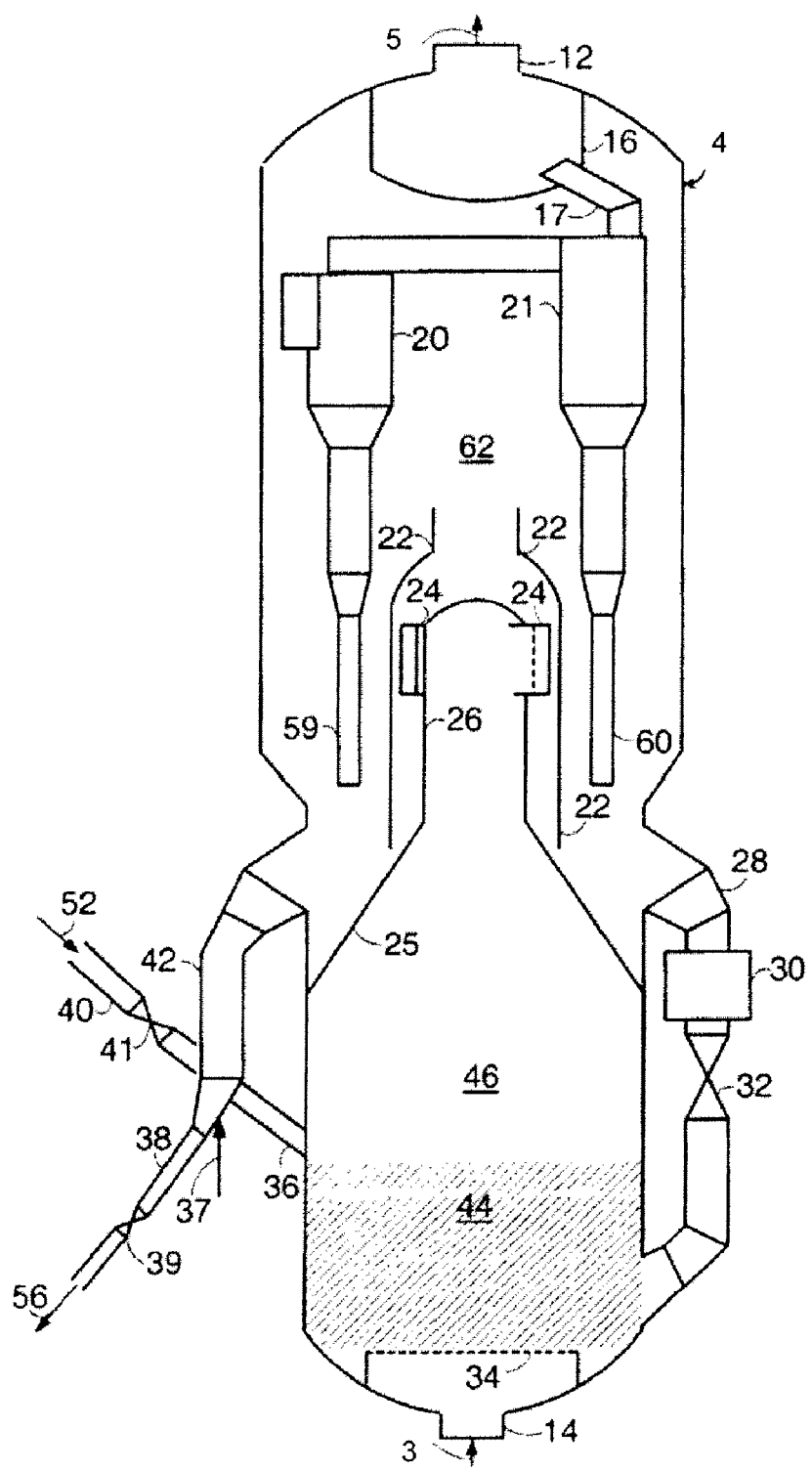
FIG. 2 is a schematic drawing of a reactor of the present invention.

Referring now to FIG. 2, the back-mixed fluidized bed reactor 4 for the dehydrogenation of alkanes is illustrated in schematic form. The back-mixed fluidized bed reactor 4 comprises a disengaging zone 62 and a lower reaction zone consisting of a dense phase zone 44 and a transition phase zone 46. A vapor phase feed comprising one or more alkanes enters via the line 3 to a feed inlet 14. The vapor phase feed passes through a feed distributor 34 and enters the dense phase zone 44. The feed distributor 34 comprises a sieve plate which permits the vapor phase feed to pass through while retaining a catalyst above the sieve plate. The catalyst in the dense phase zone 44 and the transition phase zone 46 comprises a suitable catalyst for dehydrogenation of paraffinic hydrocarbons. Suitable catalysts are well known to those skilled in the art and typically comprise a support material chosen from the group comprising: alumina, silica, aluminosilicates, aluminophosphates, natural and synthetic zeolites, clays and metal oxides on which is dispersed a metal from the group comprising iron, nickel, chromium, molybdenum, tungsten, palladium, platinum, rhenium and cobalt.

The dense phase zone 44 is operated in a regime of fluidization characterized by extensive back-mixing of the fluidized (solids) phase, such that the temperature of the catalyst is substantially uniform at all points in the dense phase zone 44. As the vapor phase feed enters the dense phase zone 44, the vapor phase feed contacts the catalyst and reacts at effective conditions to produce a dehydrogenation reactor product stream. The dehydrogenation reactor product stream comprises alkenes, unconverted alkanes and hydrogen. In the course of the reaction, a carbonaceous deposit is produced on the catalyst, reducing the activity of the catalyst. The dehydrogenation reactor product stream and a catalyst mixture comprising active catalyst and some deactivated catalyst are conveyed into the transition phase zone 46 in an intermediate portion of the lower reaction zone. As the dehydrogenation reactor product stream and the catalyst mixture continue moving upwardly through the lower reaction zone into a riser section 26, the cross-sectional area of the flow path through the back-mixed fluidized bed reactor 4 is reduced from the cross-sectional area of the dense phase zone 44 by a reducing means 25, or cone section, to the cross-sectional area of the riser section 26. In the back-mixed fluidized bed reactor 4, the superficial velocity through the transition phase zone 46 varies between about 1 and 3 meters per second (about 3 to about 10 feet per second). The riser section 26 has a smaller diameter and a smaller cross-sectional area than the dense phase zone 44 which increases the superficial velocity through the riser section 26 relative to that through the dense phase zone 44. Because the superficial velocities in the riser section 26 are higher for the same feed rate, the cross-sectional area of the overall back-mixed fluidized bed reactor 4 can be decreased by about a factor of 2 or 3 times compared to the cross-sectional area of a bubbling bed reactor. In addition, the back-mixed fluidized bed lower reaction zone provides more precise control of the feedstock and catalyst rates without the need for external catalyst addition or removal. As a result, the back-mixed fluidized bed reaction system of the present invention provides significantly decreased catalyst inventories over a traditional bubbling bed reactor.

The dehydrogenation reactor product stream and catalyst mixture continue to be conveyed through the riser section 26. The riser section 26 discharges the dehydrogenation reactor product stream and catalyst mixture through a separation zone comprising distributor arms 24, or discharge opening, and a separation vessel 22. The discharge opening 24 tangentially discharges the dehydrogenation reactor product stream and catalyst mixture to create a centripetal acceleration of the catalyst mixture and a vapor portion of the dehydrogenation reactor product stream within the separation vessel 22 that provides an initial stage cyclonic separation. The catalyst mixture falls to the bottom of the disengaging zone 62 which defines a particle outlet for discharging fluidized catalyst particles and the vapor portion of the dehydrogenation reactor product stream passes upwardly through a gas recovery outlet 23 for withdrawing gaseous fluids from the separation vessel 22. The vapor portion of the dehydrogenation reactor product, comprising entrained catalyst, continues upwards to a dilute phase separator typically in the form of a series of one to three conventional cyclone separation stages shown in the drawing as 20 and 21. The cyclone separation stage 20 represents a primary cyclone separation wherein a primary cyclone vapor stream is passed to the secondary cyclone separation stage 21 and the secondary vapors from the secondary cyclone separation stage 21 are conveyed via a conduit 17 to a plenum chamber 16. A net dehydrogenation reactor product stream comprising less than about 100 ppm-wt catalyst is withdrawn via the line 5 from a reactor outlet 12. Preferably, the net dehydrogenation reactor product stream withdrawn from the fast-fluidized bed lower reaction zone comprises less than about 70 ppm-wt catalyst. Catalyst separated in the primary cyclone separation stage 20 drops through a dip leg 59 into the bottom of the disengaging zone 62. Catalyst separated from the dehydrogenation reactor product stream in the secondary cyclone separation stage falls through a dip leg 60 into the bottom of the disengaging zone 62. The dip legs 59 and 60 are fitted with flapper valves (not shown) at their base to prevent the back flow of vapors through the cyclone separation stages 20 and 21. Catalyst accumulated in the bottom of the disengaging zone 62 is allowed to achieve an upper catalyst level and any excess catalyst is passed through at least one external catalyst recirculation standpipe 28 through a recirculation slide valve 32, and returned to the dense phase zone 44. Preferably, at least two external catalyst recirculation standpipes are employed to return catalyst from the disengaging zone 62 to the dense phase zone 44. Optionally, a heat transfer zone 30 is disposed in the external catalyst recirculation standpipe 28 at a point above the recirculation slide valve 32. The use of the heat transfer zone 30 allows the addition of heat to the circulating catalyst to meet the needs of the endothermic reactions taking place in the lower reaction zone. As the reaction proceeds, the activity of the catalyst in the lower reaction zone gradually is reduced by the buildup of coke on the catalyst. To maintain the conversion and selectivity of the reaction at acceptable levels, a portion of the catalyst mixture is withdrawn as a spent catalyst stream from the upper disengaging zone 62 and passed through a spent catalyst standpipe 42. In the spent catalyst standpipe 42, the spent catalyst stream is stripped with a stripping medium such as steam introduced in a line 37 to produce a stripped catalyst stream 56. The spent catalyst standpipe 42 will typically include a stripping section that contains grids or baffles to improve contact between the spent catalyst stream 56 and the stripping medium. The stripped catalyst stream 56 is conveyed through a line 38 and a spent catalyst slide valve 39. The stripped catalyst stream 56 is passed to a catalyst regeneration zone (not shown). In the catalyst regeneration zone, the spent catalyst stream 56 is at least partially regenerated either by oxidation or reduction to produce a regenerated catalyst stream 52. Such regeneration schemes are well known to those skilled in the art of fluidized bed reaction systems. The regenerated catalyst stream 52 is returned to the lower reaction zone via a regenerated catalyst standpipe comprising a line 40, a regenerated catalyst slide valve 41, and a line 36 to a point above the dense phase zone 44. The regenerated catalyst return is shown at a point above the dense phase zone 44. The return of the regenerated catalyst stream 52 to the lower reaction zone may be provided at any point in the riser section 26 or any portion of the back-mixed fluidized catalyst bed. Preferably, the dense phase zone 44 is operated to maintain a bed height of between about 2 meters (7 feet) and about 6 meters (20 feet) above the feed distributor 34 and below the intermediate portion of the lower reaction zone in the dense phase zone 44. More preferably, the bed height of the dense phase zone 44 comprises between about 2.4 meters (8 feet) and about 4 meters (13 feet).

EXAMPLE

An engineering simulation was used to develop a comparison of the present invention to the conventional moving bed reactor system to illustrate the advantages of the present invention.

In the base case process of the prior art, a mixture of hydrogen and propane is fed to a system of four adiabatic reactors with interheaters between each reactor. The temperature at the inlet of each reactor is 655° C. The pressure at the outlet of the final reactor is 170 kPa (10 psig). The process achieves a conversion of 40% of the propane, with 84% molar selectivity to propylene (moles of propylene formed per mole of propane reacted). In the process of the invention a mixture of hydrogen and propane is fed to a single-stage back-mixed reactor with inlet temperature of 632° C. and outlet pressure of 170 kPa (10 psig). The process achieves a conversion of 40% of the propane with 96% molar selectivity to propylene.

Although a preferred embodiment of the present invention has been described, it will be understood by those skilled in the art that other embodiments are envisioned. For example, it would be possible to use more than one back-mixed fluidized bed reactor.

The invention claimed is:

1. A catalytic dehydrogenation process for dehydrogenating an alkane stream comprising:
   a) contacting the alkane stream with a back-mixed fluidized bed of catalyst;
   b) withdrawing deactivated catalyst from the back-mixed fluidized bed of catalyst;
   c) heating the deactivated catalyst to regenerate the catalyst by burning a fuel in a stream comprising oxygen and contacting the stream with the deactivated catalyst to heat and produce hot regenerated catalyst; and
   d) returning the hot regenerated catalyst to the back-mixed fluidized bed of catalyst.

2. The process according to claim 1 in which dehydrogenation of the alkane stream requires a heat of reaction and the hot regenerated catalyst provides the heat of reaction for dehydrogenating the alkane stream.

3. The process according to claim 1 in which the back-mixed fluidized bed of catalyst is substantially isothermal.

4. The process according to claim 1 in which the back-mixed fluidized bed of catalyst has a temperature in the range 500° to 700° C.

5. The process according to claim 1 in which the hot regenerated catalyst has a temperature in the range 10° to 200° C. hotter than a temperature of the back-mixed fluidized bed of catalyst.

6. The process according to claim 1 in which the back-mixed fluidized bed of catalyst is operated at an absolute pressure in the range 50 kPa to 500 kPa.

7. The process according to claim 1 in which the alkane stream is heated before contact with the fluidized bed of catalyst and in which the alkane stream is heated to a temperature in the range between 50° C. colder to 50° C. hotter than a temperature of the back-mixed fluidized bed of catalyst.

8. The process according to claim 1 in which a first product defined as [(catalyst mass flow rate×catalyst specific heat capacity)×(temperature of the hot regenerated catalyst−temperature of the back-mixed fluidized bed of catalyst)] is substantially equal to a second product defined as [moles of the alkane stream converted×molar heat of reaction for dehydrogenation of the alkane stream].

9. The process according to claim 1 in which the alkane stream comprises one of the following: ethane, propane, isobutane, normal butane, pentanes, hexanes, heptanes or octanes.

10. The process according to claim 1 in which the catalyst comprises a support material chosen from the group comprising: alumina, silica, aluminosilicates, aluminophosphates, natural and synthetic zeolites, clays and metal oxides on which is dispersed a metal from the group comprising iron, nickel, chromium, molybdenum, tungsten, palladium, platinum, rhenium and cobalt.

11. A process for the endothermic dehydrogenation of an alkane stream comprising:
   a) heating the alkane stream to produce a heated alkane stream;
   b) contacting the heated alkane stream with a back-mixed fluidized bed of heated catalyst in a single reactor stage;
   c) withdrawing deactivated catalyst from the back-mixed fluidized bed of heated catalyst;
   d) heating the deactivated catalyst in a fluidized bed regenerator to regenerate the deactivated catalyst by burning a fuel in a stream comprising oxygen and contacting the stream with the deactived catalyst during regeneration and produce hot regenerated catalyst; and
   e) recycling the hot regenerated catalyst to the back-mixed fluidized bed of heated catalyst at a rate sufficient to maintain the back-mixed fluidized bed at substantially isothermal conditions.

12. The process according to claim 11 in which the endothermic dehydrogenation of the alkane stream requires a heat of reaction and the hot regenerated catalyst provides the heat of reaction for dehydrogenating the alkane stream.

13. The process according to claim 11 in which the endothermic dehydrogenation of the alkane stream takes place at a reaction temperature and the alkane stream is heated to approximately the reaction temperature in step (a).

14. The process according to claim 11 in which the endothermic dehydrogenation of the alkane stream takes place at a reaction temperature substantially in the range 500° to 700° C. and the hot regenerated catalyst is recycled to the back-mixed fluidized bed of heated catalyst at a rate sufficient to maintain the back-mixed fluidized bed at substantially the reaction temperature.

* * * * *